US008508246B2

(12) United States Patent
Wakaba et al.

(10) Patent No.: US 8,508,246 B2
(45) Date of Patent: Aug. 13, 2013

(54) SUBSTRATE SURFACE INSPECTING APPARATUS AND SUBSTRATE SURFACE INSPECTING METHOD

(75) Inventors: Hiroshi Wakaba, Yokohama (JP); Yoshinori Hayashi, Yokohama (JP); Koichi Miyazono, Yokohama (JP); Yoko Ono, Yokohama (JP); Hideki Mori, Yokohama (JP); Shozo Kawasaki, Yokohama (JP)

(73) Assignee: Shibaura Mechatronics Corporation, Yokohama-shi (JP)

( * ) Notice: Subject to any disclaimer, the term of this patent is extended or adjusted under 35 U.S.C. 154(b) by 399 days.

(21) Appl. No.: 12/745,377

(22) PCT Filed: Nov. 18, 2008

(86) PCT No.: PCT/JP2008/070918
§ 371 (c)(1),
(2), (4) Date: Jul. 8, 2010

(87) PCT Pub. No.: WO2009/072389
PCT Pub. Date: Jun. 11, 2009

(65) Prior Publication Data
US 2010/0310152 A1     Dec. 9, 2010

(30) Foreign Application Priority Data
Dec. 3, 2007   (JP) ................................ 2007-311983

(51) Int. Cl.
*G01R 31/01* (2006.01)
*G01R 31/00* (2006.01)
*G01R 31/308* (2006.01)
*G01R 31/28* (2006.01)

(52) U.S. Cl.
CPC ........ *G01R 31/2887* (2013.01); *G01R 31/2886* (2013.01); *G01R 31/2891* (2013.01)
USPC ............. 324/750.22; 324/750.16; 324/750.23

(58) Field of Classification Search
None
See application file for complete search history.

(56) References Cited

U.S. PATENT DOCUMENTS
2002/0014003 A1*    2/2002   Asai et al. ....................... 29/740

FOREIGN PATENT DOCUMENTS
JP     2007-147441     6/2007

* cited by examiner

*Primary Examiner* — Ryan Zeender
*Assistant Examiner* — H Rojas
(74) *Attorney, Agent, or Firm* — Kratz, Quintos & Hanson, LLP (57) ABSTRACT

A substrate surface inspection apparatus and method enabling judgment and analysis of the state of even portions of a substrate supported by supports using a captured image are provided. A support mechanism 20 is used where positions of arrangement of substrate support positions along the direction perpendicular to a scan direction by a plurality of first supports 23a to 23d are set outside the image capturing ranges of the substrate 10 by the imaging units 30a, 30b at the first relative position and inside the common image capturing range and where positions of arrangement of substrate support positions along the direction perpendicular to the scan direction by the plurality of second supports 24a to 24d are set outside the image capturing ranges of the substrate by the imaging units at the second relative position and inside the common image capturing range. The surface of the substrate 10 supported by the plurality of first supports is scanned and captured by the imaging units at the first relative position, the imaging units are moved to the second relative position, then the surface of the substrate 10 supported by the plurality of second supports is scanned and captured by the imaging units at the second relative position.

7 Claims, 10 Drawing Sheets

SUBSTRATE SURFACE INSPECTING APPARATUS AND SUBSTRATE SURFACE INSPECTING METHOD

TECHNICAL FIELD

The present invention relates to a substrate surface inspection apparatus and substrate inspection method capturing an image of the surface of a semiconductor wafer or other substrate for inspection.

BACKGROUND ART

In the past, an apparatus capturing an image of the surface of a semiconductor wafer for inspection has been proposed (see Patent Citation 1). This inspection apparatus is structured by a stage carrying a semiconductor wafer faced by a carriage housing a line sensor and a light source (LED) (optical block). Further, it is designed so that, in the process of the carriage moving in a predetermined direction above the semiconductor carried on the stage, the line sensor scans the surface of the semiconductor wafer to capture an image. According to such an inspection apparatus, the captured image obtained based on the image signal from the line sensor scanning the surface of the semiconductor wafer can be used to visually inspect the surface of the semiconductor wafer. Further, by processing the captured image, it is also possible to analyze damage, defects, etc.

Patent Citation 1: Japanese Patent Publication (A) No. 2007-147441

DISCLOSURE OF INVENTION

Technical Problem

However, the above-mentioned such conventional inspection apparatus is structured with the semiconductor wafer carried on a stage, so there was a possibility of the surface of the semiconductor wafer which abuts against the stage (back surface) being contaminated by foreign matter or being damaged.

Therefore, it has been considered not to place the semiconductor wafer (substrate) under inspection on a stage, but to support its edges by a plurality of supports and scan its surface to capture its image in that state. However, if supporting the edges of a substrate by a plurality of supports and scanning the surface of the substrate in that state, the plurality of supports supporting the edges of the substrate will end up being superimposed in the captured image and the portions which the supports support will end up being obscured by the images of the supports, so the states of those portions will not be able to be judged and analyzed from the captured image.

The present invention was made in view of this situation and provides a substrate surface inspection apparatus and substrate surface inspection method which, even when using a plurality of supports to support the edges and capturing an image of the surface of the substrate in that state, enable judgment and analysis from the captured image of even portions which the supports support.

Technical Solution

The substrate surface inspection apparatus according to the present invention is a substrate surface inspection apparatus capturing an image of a surface of a substrate and inspecting the substrate based on the obtained image, having a support mechanism provided with a plurality of first supports and a plurality of second supports able to support edges of the substrate and release the same, an imaging unit arranged facing the surface of the substrate supported by either the group of the plurality of first supports and the group of the plurality of second supports in the support mechanism, a scan movement mechanism making the imaging unit and the support mechanism move relative to each other so that the imaging unit scans and captures an image of the surface of the substrate in a predetermined scan direction, and a shift movement mechanism making the imaging unit and the support mechanism move in a direction traversing the scan direction between a first relative position and a second relative position; the imaging unit able to capture, at the first relative position and the second relative position, images from a predetermined region at one side of the substrate and from a predetermined region at the other side, the predetermined regions including a common image capturing range, the common image capturing range defined as a predetermined range of the substrate at the first relative position and the second relative position in a direction perpendicular to the scan direction, positions of arrangement of substrate support positions along the direction perpendicular to the scan direction by the plurality of first supports in the support mechanism being set outside the image capturing range of the substrate by the imaging unit at the first relative position and inside the common image capturing range, and positions of arrangement of substrate support positions along the direction perpendicular to the scan direction by the plurality of second supports in the support mechanism being set outside the image capturing range of the substrate by the imaging unit at the second relative position and inside the common image capturing range.

Due to this configuration, the support of the substrate by the plurality of second supports of the support mechanism can be withdrawn, then the surface of the substrate supported by the plurality of first supports can be scanned and captured by the imaging unit in the first relative position with respect to the support mechanism in that state. In this case, the first supports in the common image capturing range of the substrate of the imaging unit are superimposed in the obtained captured image. Further, the imaging unit at the first relative position with respect to the support mechanism can be moved by the shift mechanism from the first relative position to the second relative position. Further, the support of the substrate by the plurality of first supports of the support mechanism can be withdrawn, then the surface of the substrate supported by the plurality of second supports can be scanned and captured by the imaging unit in the second relative position with respect to the support mechanism in that state. In this case, the second supports in the common image capturing range of the substrate of the imaging unit can be superimposed in the obtained captured image. In this way, it is possible to obtain a captured image in which the first supports are superimposed at portions corresponding to the common image capturing range of the substrate by the imaging unit (no second supports) and with the first supports not superimposed at the other portions and a captured image in which the second supports are superimposed at portions corresponding to the common image capturing range (no first supports) and with the second supports not superimposed at the other portions.

Further, the substrate surface inspection apparatus according to the present invention may be configured so that the imaging unit is set fixed in position, and the scan movement mechanism makes the support mechanism move in a direction opposite to the scan direction.

Due to this configuration, it becomes possible for a fixed position imaging unit to scan in the scan direction the surface of a substrate supported by either a group of a plurality of first supports and a group of a plurality of second supports in the support mechanism.

Further, the substrate surface inspection apparatus according to the present invention may be configured so that the shift movement mechanism makes the support mechanism move between the first relative position and the second relative position.

Due to this configuration, it is possible to make the fixed position imaging unit move relative to the support mechanism between the first relative position and the second relative position.

Further, the substrate surface inspection apparatus according to the present invention may be configured so that the imaging unit has a line sensor extending in a direction traversing the scan direction.

Due to this configuration, it is possible to successively scan the surface of a substrate supported by either the group of the plurality of first supports and the group of the plurality of second supports in the support mechanism one line at a time.

Furthermore, the substrate surface inspection apparatus according to the present invention may be configured so that the imaging unit has a first camera unit arranging facing a first surface of the substrate supported by either of the plurality of first supports and the plurality of second supports of the support mechanism and a second camera unit arranged facing a second surface of the substrate forming a back side of the first surface.

Due to this configuration, the imaging unit (first camera unit and second camera unit) can scan the substrate at the first relative position, then scan the substrate at the second relative position to thereby obtain two captured images of each of the front and back surfaces of the substrate (first surface and second surface) without turning the substrate over.

Further, the substrate surface inspection apparatus according to the present invention may be configured so that the apparatus has a first illumination unit illuminating an image capturing location of the first camera unit and a second illumination unit illuminating an image capturing location of the second camera unit, and the first illumination unit and the second illumination unit are set so that an illumination direction of light from the first illumination unit does not face the second camera unit and an illumination direction of light from the second illumination unit does not face the first camera unit.

Due to this configuration, the light of the first illumination unit illuminating the image capturing location of the first camera unit can be prevented from affecting the imaging operation of the second camera unit and the light of the second illumination unit illuminating the image capturing location of the second camera unit can be prevented from affecting the imaging operation of the first camera unit.

A substrate surface inspection method according to the present invention uses the substrate surface inspection apparatus and comprises a first imaging step of scanning and capturing an image of a surface of the substrate supported by the plurality of first supports, in a state where support of the substrate by the plurality of second supports of the support mechanism is released, by the imaging unit at a first relative position with respect to the support mechanism, a shift step of making the imaging unit move relative to the support mechanism to a second relative position after the scan at the first relative position ends, and a second imaging step of scanning and capturing an image of a surface of the substrate supported by the plurality of second supports, in a state where support of the substrate by the plurality of first supports of the support mechanism is released, by the imaging unit at a second relative position with respect to the support mechanism.

Due to this configuration, due to the scan of the imaging unit at the first relative position, a captured image in which the first supports are superimposed at portions corresponding to the common image capturing range of the substrate by the imaging unit (no second supports) and with the first supports not superimposed at the other portions is obtained, while due to the scan of the imaging unit at the second relative position, a captured image in which the second supports are superimposed at portions corresponding to the common image capturing range (no first supports) and with the second supports not superimposed at the other portions is obtained.

Further, the substrate surface inspection method according to the present invention may be configured so that the scan direction of the imaging unit with respect to the substrate in the first imaging step and the scan direction of the imaging unit with respect to the substrate in the second imaging step are set to be opposite.

Due to this configuration, after the scan of the substrate by the relative movement of the imaging unit and support mechanism at the first relative position ends, it becomes possible to scan the substrate at the second relative position by making the imaging unit and support mechanism move in opposite directions at the second position.

Advantageous Effects

According to the substrate surface inspection apparatus and substrate surface inspection method according to the present invention, a captured image in which the first supports are superimposed at portions corresponding to the common image capturing range of the substrate by the imaging unit (no second supports) and with the first supports not superimposed at the other portions and a captured image in which the second supports are superimposed at portions corresponding to the common image capturing range (no first supports) and with the second supports not superimposed at the other portions can be obtained, so assuming that the support positions of the edges of the substrate by the plurality of first supports and the plurality of second supports differ, it is possible to judge and analyze portions of the substrate supported by the first supports from the captured image where the second supports are superimposed at portions corresponding to the common image capturing range and, further, it is possible to judge and analyze portions of the substrate supported by the second supports from the captured image where the first supports are superimposed at portions corresponding to the common image capturing range.

Note that, "superimpose" means the state where the image concerned obscures another image. For example, "the first supports are superimposed" means that the images of the first supports obscure the images of the portions of the substrate supported by the first supports and does not mean the state where that the images of the first supports are merely superimposed.

EXPLANATION OF REFERENCES 10 semiconductor wafer (substrate)
20 support mechanism
21 ring-shaped frame
22a, 22b support legs
23a, 23b, 23c, 23d first supports
24a, 24b, 24c, 24d second supports
25 group of first actuators
25a, 25b, 25c, 25d first actuators
26 group of second actuators
26a, 26b, 26c, 26d second actuators
30a first camera unit
30b second camera unit
31a first illumination unit
31b second illumination unit
50 base
51a, 52a, 51b, 52b scan direction guide grooves
53, 54 shift direction guide grooves
55 frame
60 carriage (scan movement mechanism)
70 shift movement mechanism
71 stage
72 drive unit
100 processing unit
111 operating unit
112 display unit
120 drive control unit

BEST MODE FOR CARRYING OUT THE INVENTION

Below, embodiments of the present invention will be explained using the drawings.

Figure 1:
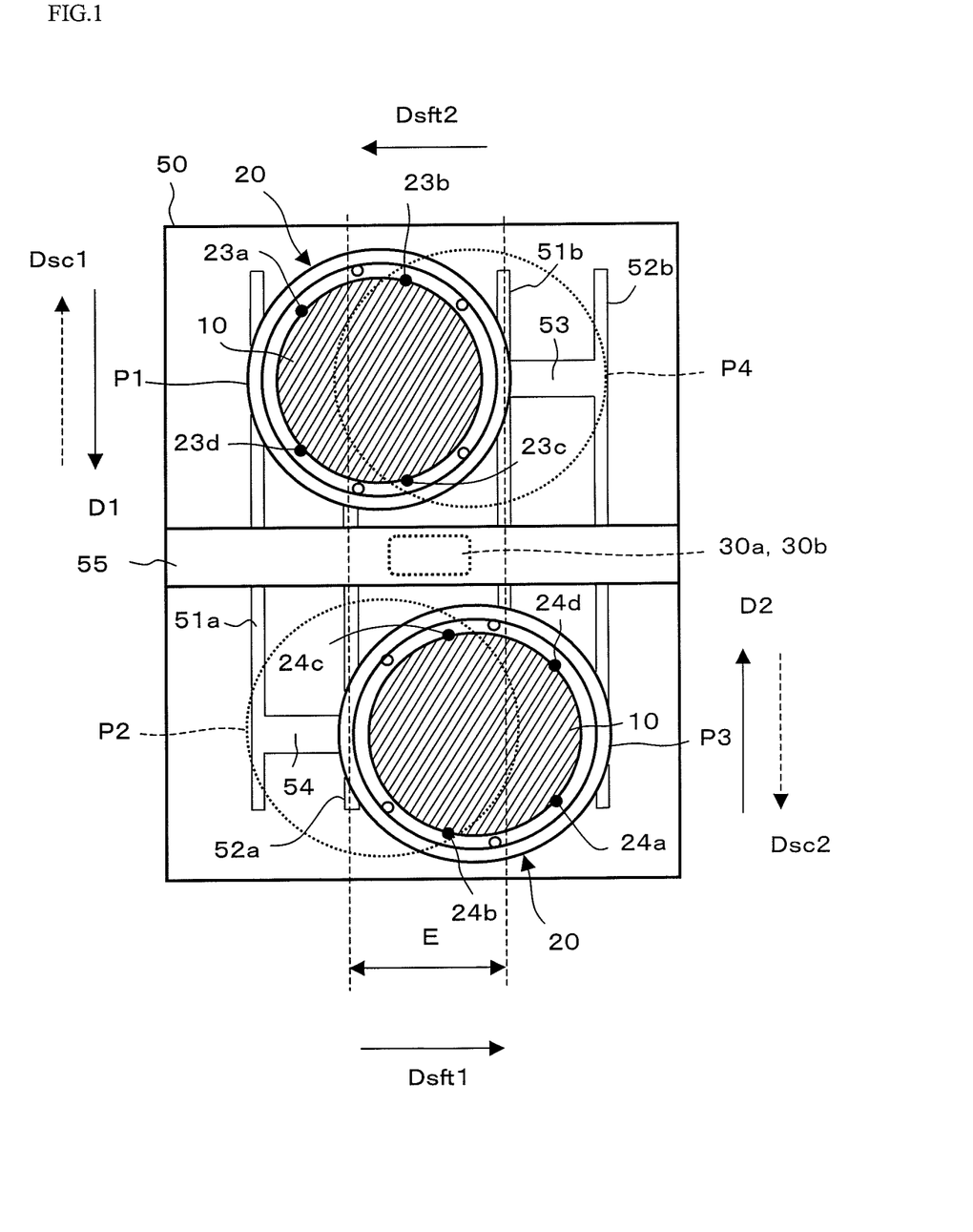
FIG. 1 A plan view showing a substrate surface inspection apparatus according to one embodiment of the present invention.
Figure 2:
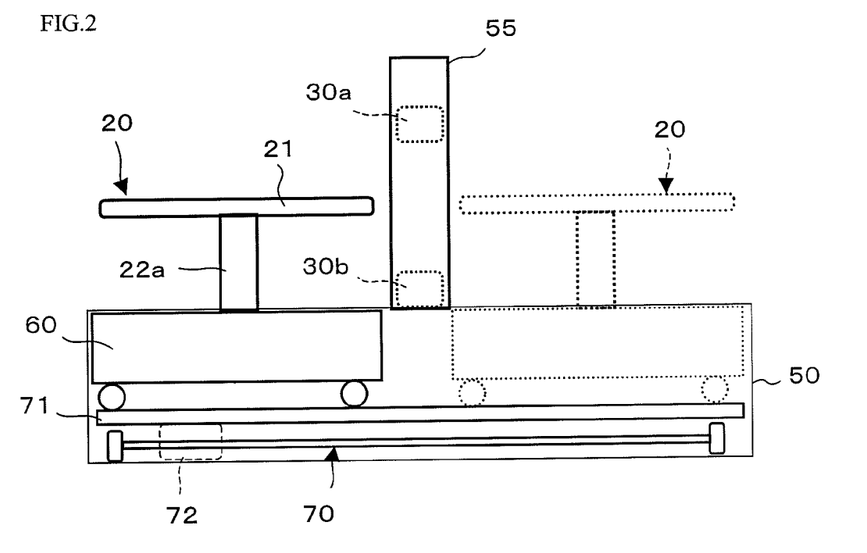
FIG. 2 A side view showing a substrate surface inspection apparatus according to one embodiment of the present invention.
Figure 3:
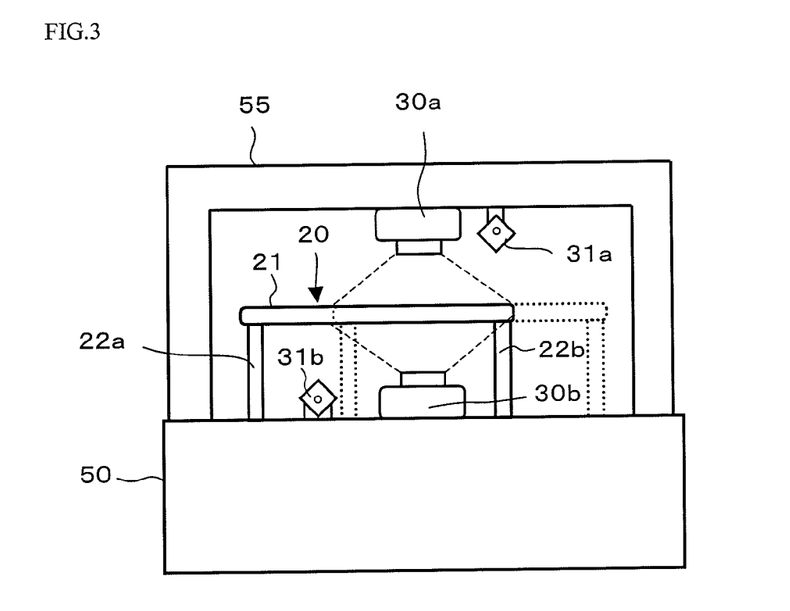
FIG. 3 A front view showing a substrate surface inspection apparatus according to one embodiment of the present invention.

The substrate surface inspection apparatus according to one embodiment of the present invention is configured as shown in FIG. 1 to FIG. 3. This substrate surface inspection apparatus is a semiconductor wafer surface inspection apparatus for inspecting semiconductor wafers. FIG. 1 is a plan view of the same, FIG. 2 is a side view of the same, and FIG. 3 is a front view of the same.

In FIG. 1 to FIG. 3, this inspection apparatus has a base 50. Inside this base 50, a carriage 60 (scan movement mechanism) and a shift movement mechanism 70 are provided (in particular, see FIG. 2). The shift movement mechanism 70 has a stage 71. The carriage 60 is designed to be able to move back and forth on the stage 71 on its own power (up-down direction movement in FIG. 1 and left-right direction movement in FIG. 2). The shift movement mechanism 70, further, has a drive unit 72 including a motor, gear mechanism, etc. This drive unit 72 enables the stage 71 to move in a direction perpendicular to the direction of movement of the carriage 60 under its own power (left-right direction in FIG. 1 and FIG. 3).

The carriage 60 is provided with a support mechanism 20 supporting a semiconductor wafer (below, simply referred to as a "wafer") 10 under inspection. This support mechanism 20 sticks out from the top surface of the base 50. The support mechanism 20 has a ring-shaped frame 21 and two support legs 22a, 22b supporting the ring-shaped frame 21 aligned in a direction perpendicular to the direction of movement of the carriage 60. These support legs 22a, 22b are fixed to the carriage 60. At the top surface of the base 50, two groups of scan direction guide grooves 51a, 51b and 52a, 52b extending in the direction of movement of the carriage 60 are formed in parallel. On the top surface of the base 50, furthermore, at two locations near the ends of one side of the two sets of scan direction guide grooves 51a, 51b and 52a, 52b and near the ends of the other side, shift direction guide grooves 53, 54 are formed between the scan direction guide grooves 51a and 52b positioned at the outermost sides so as to perpendicularly intersect the scan direction guide grooves.

Due to the two groups of scan direction guide grooves 51a, 51b and 52a, 52b formed on the top surface of the base 50 in this way, at the time of self powered movement of the carriage 60, the two support legs 22a, 22b of the support mechanism 20 are guided by one group of scan direction guide grooves 51a, 51b or by the other group of scan direction guide grooves 52a, 52b. Further, in the state with the two support legs 22a, 22b of the support mechanism 20 positioned at the shift direction guide groove 53 or 54, at the time of movement in a direction perpendicular to the self powered movement of the carriage 60 accompanying movement of the shift movement mechanism 70, the two support legs 22a, 22b of the support mechanism 20 are guided by the shift direction guide groove 53 or 54.

At the approximate center location between the shift direction guide grooves 53 and 54 formed at the top surface of the base 50, an arch shaped frame 55 is provided. At the approximate center portion of this frame 55, a first camera unit 30a is attached facing downward. Between the scan direction guide grooves 52a and 51b on the top surface of the base 50, a second camera unit 30b is set so as to face the first camera unit 30a. Further, near the mounting position of the first camera unit 30a on the frame 55, a first illumination unit 31a is mounted illuminating an image capturing location of the first camera unit 30a at the front surface (below, called the "first surface") of the wafer 10 supported by the support mechanism 20 moving over the base 50. Near the set position of the second camera unit 30b at the top surface of the base 50, a second illumination unit 31b is mounted illuminating an image capturing location of the second camera unit 30b at the back surface (below, called the "second surface") opposite to the first surface of the wafer 10 supported by the support mechanism 20 moving over the base 50. The first camera unit 30a and second camera unit 30b have line sensors extending in directions perpendicularly intersecting the scan direction guide grooves 51a, 51b, 52a, 52b. Their image capturing ranges are determined by the lengths of the line sensors, lenses, and other parts of the optical systems etc.

The orientation of the first illumination unit 31a is set so as to effectively illuminate the image capturing range of the first camera unit 30a while preventing the direction of illumination of light from the first illumination unit 31a from facing the second camera unit 30b. Further, the orientation of the second illumination unit 31b is also set so as to effectively illuminate the image capturing range of the second camera unit 30b while preventing the direction of illumination of light from the second illumination unit 31b from facing the first camera unit 30a. Due to this, the light of the first illumination unit 31a illuminating the image capturing location of the first camera unit 30a can be kept from affecting the image capturing operation by the second camera unit 30b, while the light of the second illumination unit 31b illuminating the image capturing location of the second camera unit 30b can be kept from affecting the image capturing operation by the first camera unit 30a.

When the support mechanism 20 is positioned so that the support legs 22a, 22b are guided by one group of scan direction guide grooves 51a, 51b, as shown in FIG. 1, along with movement of the support mechanism 20 in a first direction D1 along the scan direction guide grooves 51a, 51b, the first camera unit 30a and second camera unit 30b scan in a first scan direction Dsc1 and capture a region of about two-thirds of one side of the image capturing range E (corresponding to the length of the line sensors) including the edges of one side of the first surface and second surface of the wafer 10 supported by the support mechanism 20. At this time, the first camera unit 30a and second camera unit 30b are said to be at a "first relative position" with respect to the support mechanism 20 in the direction traversing the scan direction (in this example, direction perpendicularly intersecting it).

Further, when the support mechanism 20 is positioned so that the support legs 22a, 22b are guided by the other group of scan direction guide grooves 52a, 52b, similarly, as shown in FIG. 1, along with movement of the support mechanism 20 in a second direction D2 along the scan direction guide grooves 52a, 52b, the first camera unit 30a and second camera unit 30b scan in the second scan direction Dsc2 and capture a region of about two-thirds of one side of the image capturing range E including the edges of the other side of the first surface and second surface of the wafer 10 supported by the support mechanism 20. At this time, the first camera unit 30a and second camera unit 30b are said to be at a "second relative position" with respect to the support mechanism 20 in the direction traversing the scan direction (in this example, direction perpendicularly intersecting it).

A more detailed structure of the support mechanism 20 will be explained with reference to FIG. 4, FIG. 5, and FIG. 6. Note that, FIG. 4 and FIG. 6 are plan views showing the support mechanism 20, while FIG. 5 is a cross-sectional view along the line A-A in FIG. 4.

Figure 4:
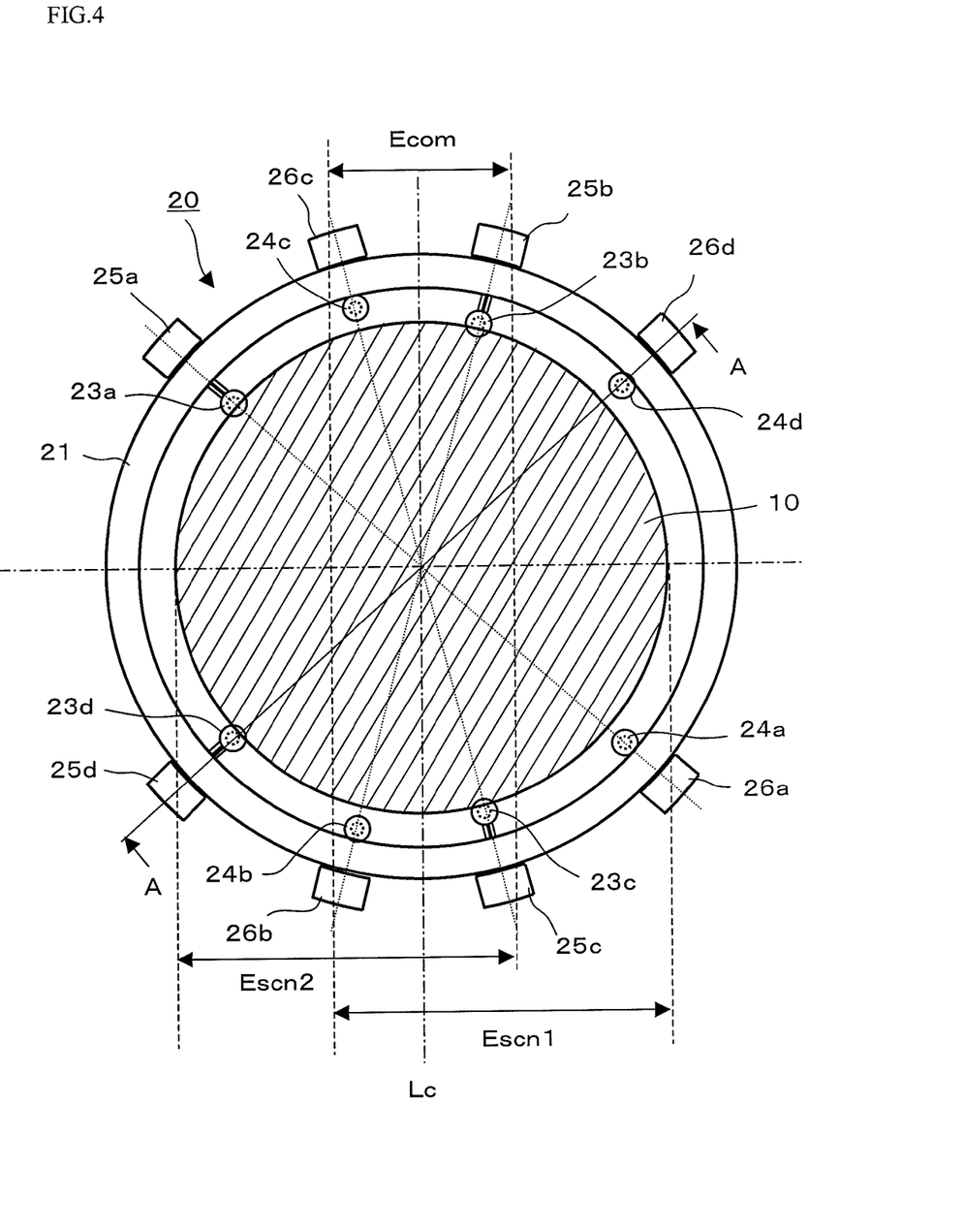
FIG. 4 A plan view showing in detail a support mechanism using first supports to support a semiconductor wafer.
Figure 5:
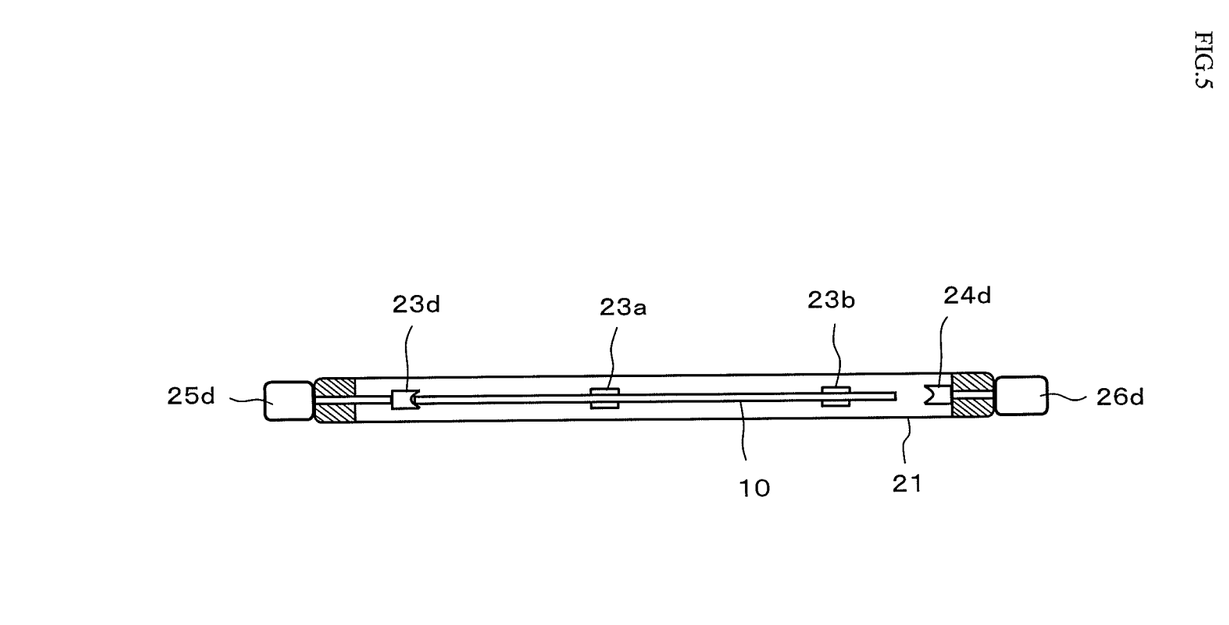
FIG. 5 A cross-sectional view showing an A-A cross-section in FIG. 4.
Figure 6:
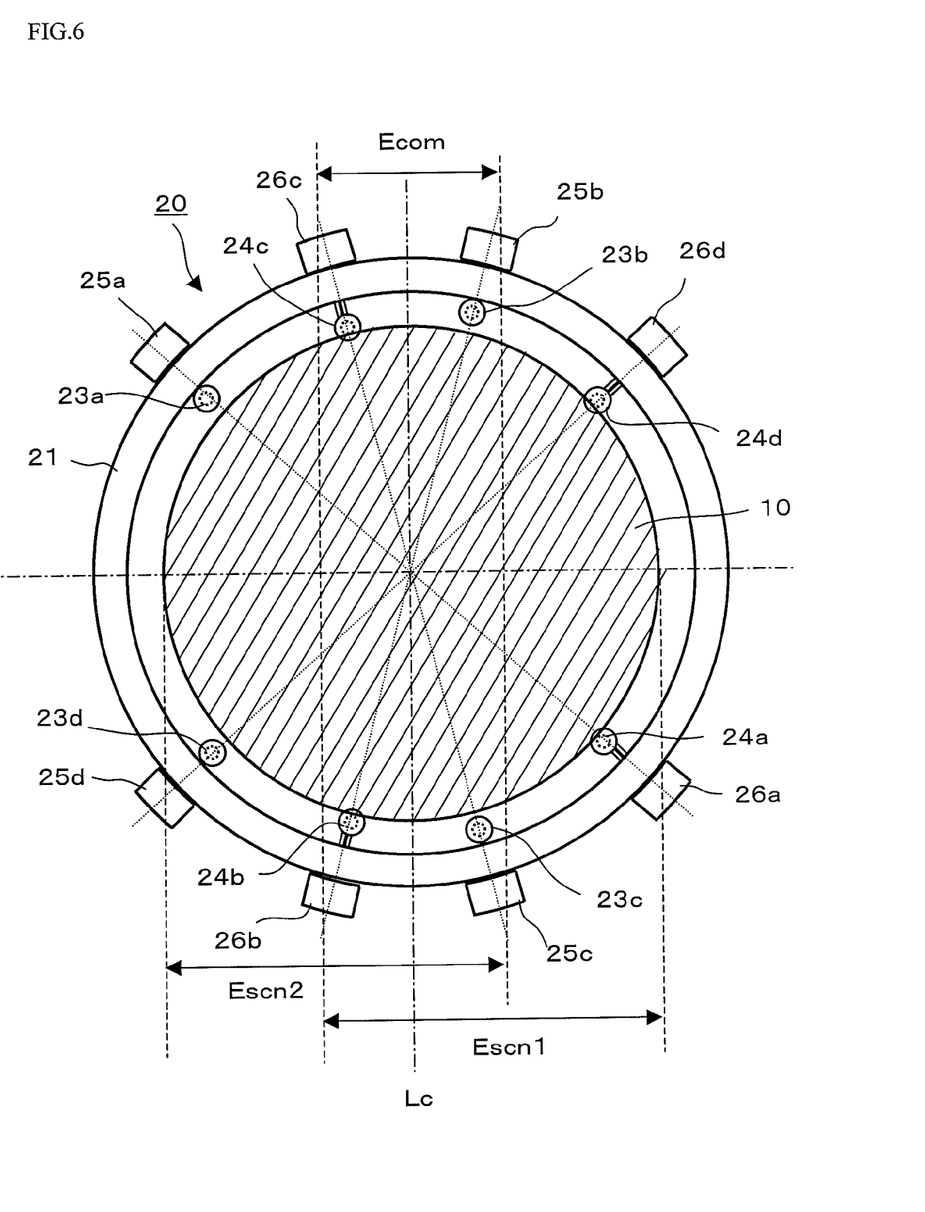
FIG. 6 A plan view showing in detail a support mechanism using second supports to support a semiconductor wafer.

In FIG. 4, FIG. 5, and FIG. 6, along the inside surface of a ring-shaped frame 21, four (a plurality of) first supports 23a, 23b, 23c, and 23d and four (a plurality of) second supports 24a, 24b, 24c, and 24d are arranged. The first supports 23a, 23b, 23c, and 23d can be deployed or retracted in the diametrical direction of the ring-shaped frame 21 by first actuators 25a, 25b, 25c, and 25d correspondingly provided at the outside surface of the ring-shaped frame 21, while the second supports 24a, 24b, 24c, and 24d can be deployed or retracted in the diametrical direction of the ring-shaped frame 21 by second actuators 26a, 26b, 26c, and 26d correspondingly provided at the outside surface of the ring-shaped frame 21. As shown in FIG. 4 and FIG. 5, when reaching a state where the first supports 23a, 23b, 23c, and 23d are deployed and the second supports 24a, 24b, 24c, and 24d are retracted, the edges of the wafer 10 are supported by the deployed first supports 23a, 23b, 23c, and 23d. On the other hand, as shown in FIG. 6, when reaching a state where the first supports 23a, 23b, 23c, and 23d are retracted and the second supports 24a, 24b, 24c, and 24d are deployed, the edges of the wafer 10 are supported by the deployed second supports 24a, 24b, 24c, and 24d.

As shown in FIG. 4 and FIG. 6, the image capturing range Escn1 of the first camera unit 30a and second camera unit 30b at the first relative position with respect to the support mechanism 20 (state of support mechanism 20 guided by one group of scan direction guide grooves 51a, 51b) in a direction perpendicularly intersecting the scan direction of the wafer 10 and the image capturing range Escn2 of the first camera unit 30a and second camera unit 30b at the second relative position with respect to the support mechanism 20 (state of support mechanism 20 guided by the other group of scan direction guide grooves 52a, 52b) in a direction perpendicularly intersecting the scan direction of the wafer 10 overlap. In this way, predetermined ranges of the of the first surface and second surface of the wafer 10 supported by the support mechanism 20 straddling a centerline Lc in the direction perpendicularly intersecting the scan direction form a common image capturing range Ecom where the image capturing ranges Escn1, Escn2 of the first camera unit 30a and second camera unit 30b at the first relative position and second relative position overlap as explained above.

Regarding the positions of arrangement of the positions of the wafer supported by the four first supports 23a, 23b, 23c, and 23d along the direction perpendicularly intersecting the scan direction, two first supports 23a, 23d are set outside the image capturing range Escn1 of the first camera unit 30a and second camera unit 30b at the first relative position, while the other two first support 23b, 23c are set in the common image capturing range Ecom. Further, regarding the positions of arrangement of the positions of the wafer supported by the four second supports 24a, 24b, 24c, and 24d along the direction perpendicularly intersecting the scan direction, two second supports 24a, 24d are set outside the image capturing range Escn2 of the first camera unit 30a and second camera unit 30b at the second relative position, while the other two second support 24b, 24c are set in the common image capturing range Ecom.

Figure 7:
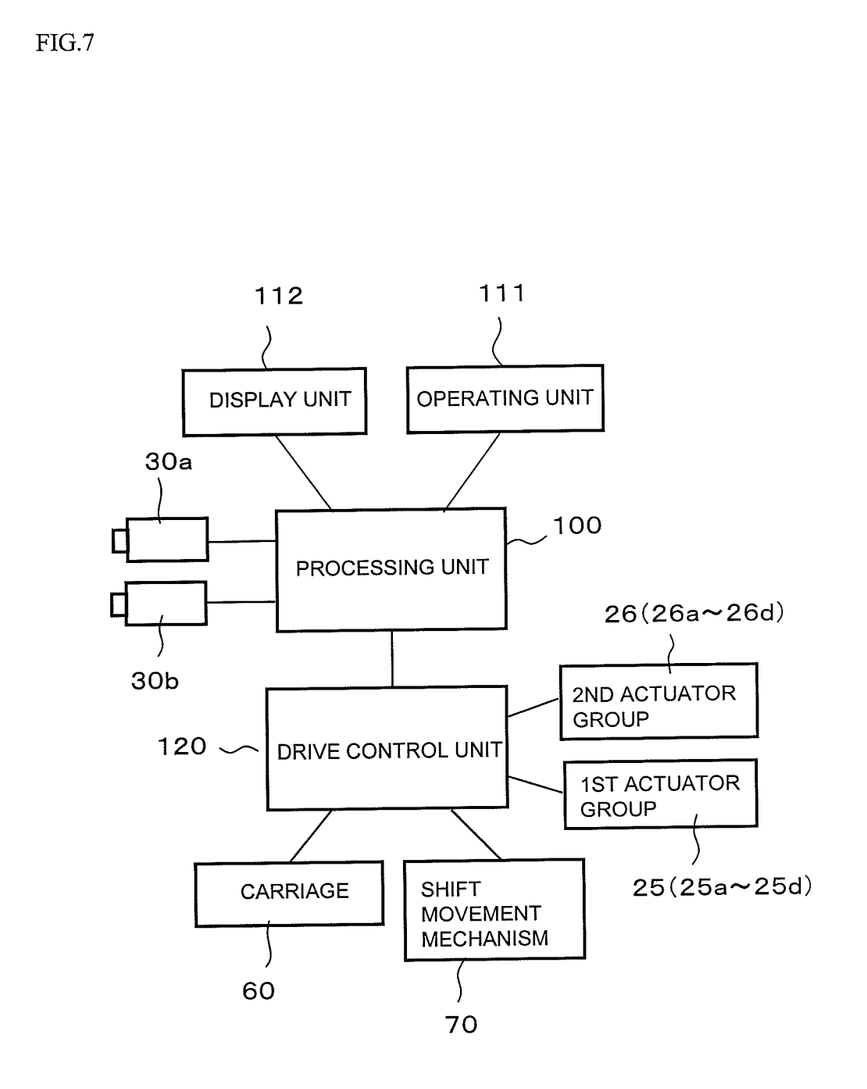
FIG. 7 A block diagram showing the basic configuration of a processing system of a substrate surface inspection apparatus according to one embodiment of the present invention.

The processing system of the inspection apparatus is configured as shown in FIG. 7.

In FIG. 7, the processing system has a processing unit 100 and a drive control unit 120. The processing unit 100 is configured by a computer, receives as input image signals from the first camera unit 30a and second camera unit 30b capturing images of the first surface and second surface of the wafer 10, generates captured images of the first surface and second surface of the wafer 10, and executes predetermined image processing. Further, the processing unit 100 is connected to an operating unit 111 and display unit 112, executes processing based on signals from the operating unit 111 operated by an operator, and, further, displays the captured images and various information obtained by various image processing on the display unit 112.

Further, the processing unit 100 controls the drive control unit 120. The drive control unit 120, under the control of the processing unit 100, controls the drive operation of the carriage 60 (scan movement mechanism) and controls the drive operation of the drive unit 72 of the shift movement mechanism 70. The drive control unit 120, furthermore, controls the drive operation of the group of first actuators 25 provided at the support mechanism 20 (first actuators 25a to 25d) (deploy/retract control of first supports 23a to 23b) and controls the drive operation of the group of second actuators 26 (second actuators 26a to 26d) (deploy/retract control of second supports 24a to 24d).

Figure 8:
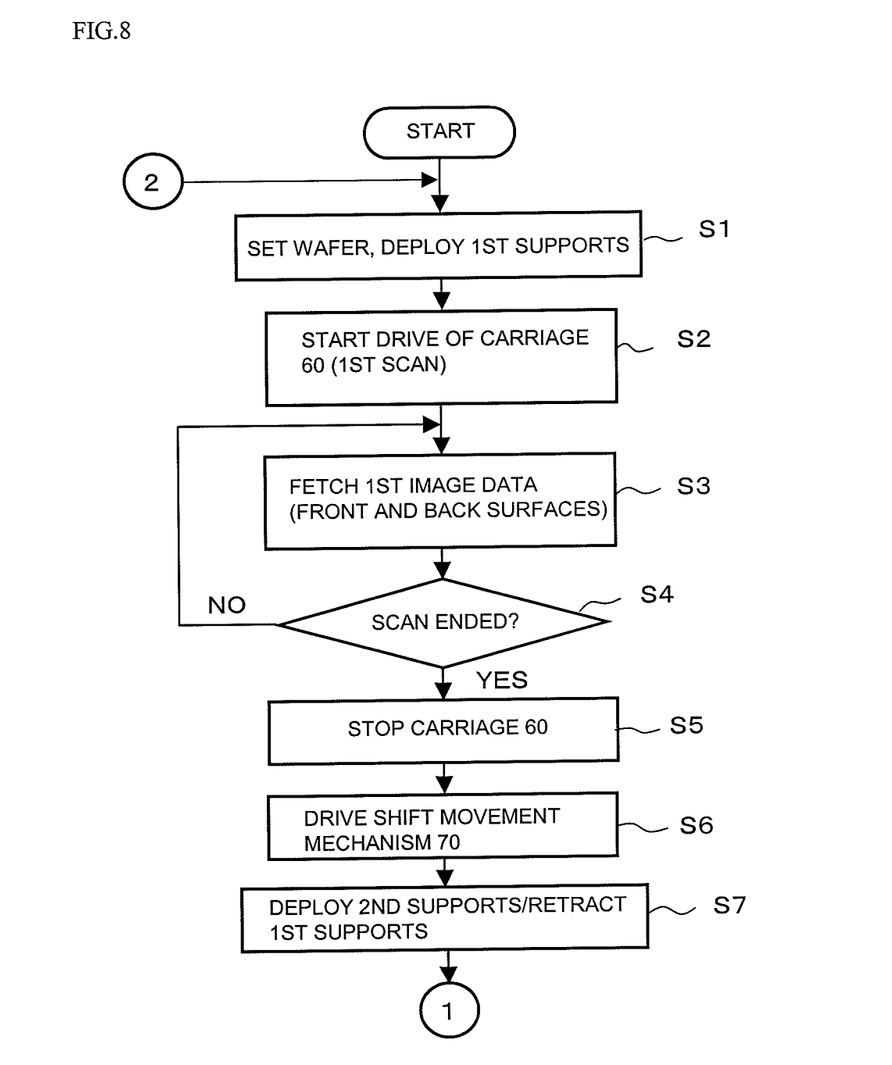
FIG. 8 A flow chart showing a processing routine at the processing unit (Part 1).

The control unit 100 executes processing in accordance with the routine shown in FIG. 8.

As the initial state, the support mechanism 20 is in a state where the support legs 22a, 22b are guided by the scan direction guide grooves 51a, 51b while positioned in the shift direction guide groove 53 so that the first camera unit 30a and second camera unit 30b become the first relative position with respect to the support mechanism 20 (see P1 in FIG. 1). In this initial state, the processing unit 100 starts the processing.

In FIG. 8, when a wafer 10 to be inspected transported by a transport mechanism (not shown) is set at a predetermined position of the support mechanism 20, the processing unit 100 instructs the deployment of the first supports 23a to 23d to the drive control unit 120 (S1). Under the control of the drive operation by the drive control unit 120 for the first actuators 25a to 25d based on this instruction, the first supports 23a to 23d are deployed and the first supports 23a to 23d support the edges of the wafer 10.

When the wafer 10 under test is supported by the first supports 23a to 23d of the support mechanism 20, the processing unit 100 instructs the start of drive of the carriage 60 to the drive control unit 120 (S2). Under the control of the drive operation by the drive control unit 120 for the carriage 60 based on this instruction, the carriage 60 at the position of P1 is guided by the scan direction guide grooves 51a, 51b and starts to move in a first direction D1 at a predetermined speed (self powered movement). Further, along with the self powered movement of the carriage 60, the support mechanism 20 passes through the image capturing range E of the first camera unit 30a and second camera unit 30b (see FIG. 1). In the process, the first camera unit 30a and second camera unit 30b individually scan and capture images of the first surface and second surface of the wafer 10, supported by the support mechanism 20 (first supports 23a to 23d), in the scan direction Dsc1 (first scan).

Due to the scan in the scan direction Dsc1 of the first camera unit 30a and second camera unit 30b at the first relative position with respect to the support mechanism 20, the image capturing range Escn1 of the first surface and second surface of the wafer 10 (see FIG. 4 and FIG. 6) is captured. The first camera unit 30a and second camera unit 30b successively output image signals. The processing unit 100 receives as input the image signals from the first camera unit 30a and second camera unit 30b and successively stores the image signals as corresponding image data (first image data) in an internal memory (S3). The processing unit 100, when judging if the carriage 60 has reached the shift direction guide groove 54 (see P2 in FIG. 1) and the scan of the wafer 10 has ended (YES at S4), gives a stop instruction of the carriage 60 to the drive control unit 120 (S5). Due to the control of the drive control unit 120 based on this stop instruction, the carriage 60 is stopped.

Figure 10:
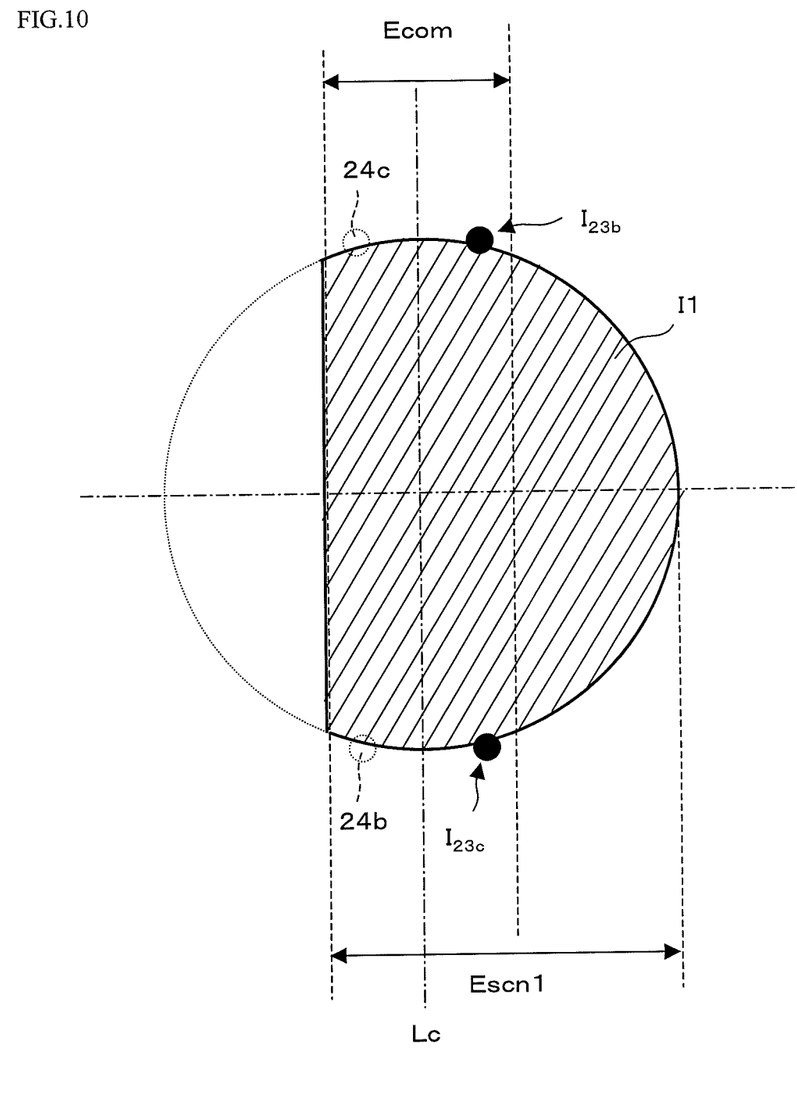
FIG. 10 A view showing an example of a captured image obtained when scanning a semiconductor wafer at a first relative position.

A first captured image I1 expressed by first image data (corresponding to image capturing range Escn1) obtained by the imaging operation of the above-mentioned first camera unit 30a and second camera unit 30b, as shown in FIG. 10, has the first supports 23b, 23c arranged in the common image capturing range Ecom superimposed in it. Due to those image parts $I_{23b}$, $I_{23c}$, the first captured image I1 is partially obscured. That is, the portions of the wafer 10 supported by the first supports 23b, 23c are obscured by the images of the first supports 23b, 23c in this state. However, the second supports 24a to 24d of the support mechanism 20 are retracted in this state, so the first captured image I1 does not have the second supports 24b, 24c arranged at Ecom in the common image capturing range superimposed in it. Further, the other first supports 23a, 23d are arranged outside of the image capturing range Escn1, so these are also not superimposed in the first captured image I1.

Returning to FIG. 8, when the first image data finishes being acquired and the carriage 60 is stopped (S5), the processing unit 100 gives a drive instruction of the shift movement mechanism 70 to the drive control unit 120 (S6). Under the control of the drive operation by the drive control unit 120 for the shift movement mechanism 70 based on this instruction, the shift movement mechanism 70 (stage 71) moves in the first shift direction Dsft1 (see FIG. 1). Due to the movement of the carriage 60 accompanying movement of this shift movement mechanism 70, the support mechanism 20 moves in the first shift direction Dsft1 while the support legs 22a, 22b are guided by the shift direction guide groove 54 until the first camera unit 30a and second camera unit 30b are positioned at the second relative position. When the support mechanism 20 reaches the other scan direction guide grooves 52a, 52b and the first camera unit 30a and second camera unit 30b are positioned at the second relative position with respect to the support mechanism 20 (see P3 in FIG. 1), the processing unit 100 instructs the deployment of the second supports 24a to 24d and the retraction of the first supports 23a to 23b to the drive control unit 120 (S7). Under the control of the drive operation by the drive control unit 120 for the first actuators 25a to 25d and second actuators 26a to 26d based on this instruction, the second supports 24a to 24d are deployed, the first supports 23a to 23d are retracted, and the edges of the wafer 10 become supported by the second supports 24a to 24d instead of the first supports 23a to 23d. At this time, due to the deployment of the first supports 24a to 24d, the edges of the wafer 10 are supported. After that, if making the first supports 23a to 23d retract, the wafer 10 will be protected against positional deviation, so this is preferred.

Figure 9:
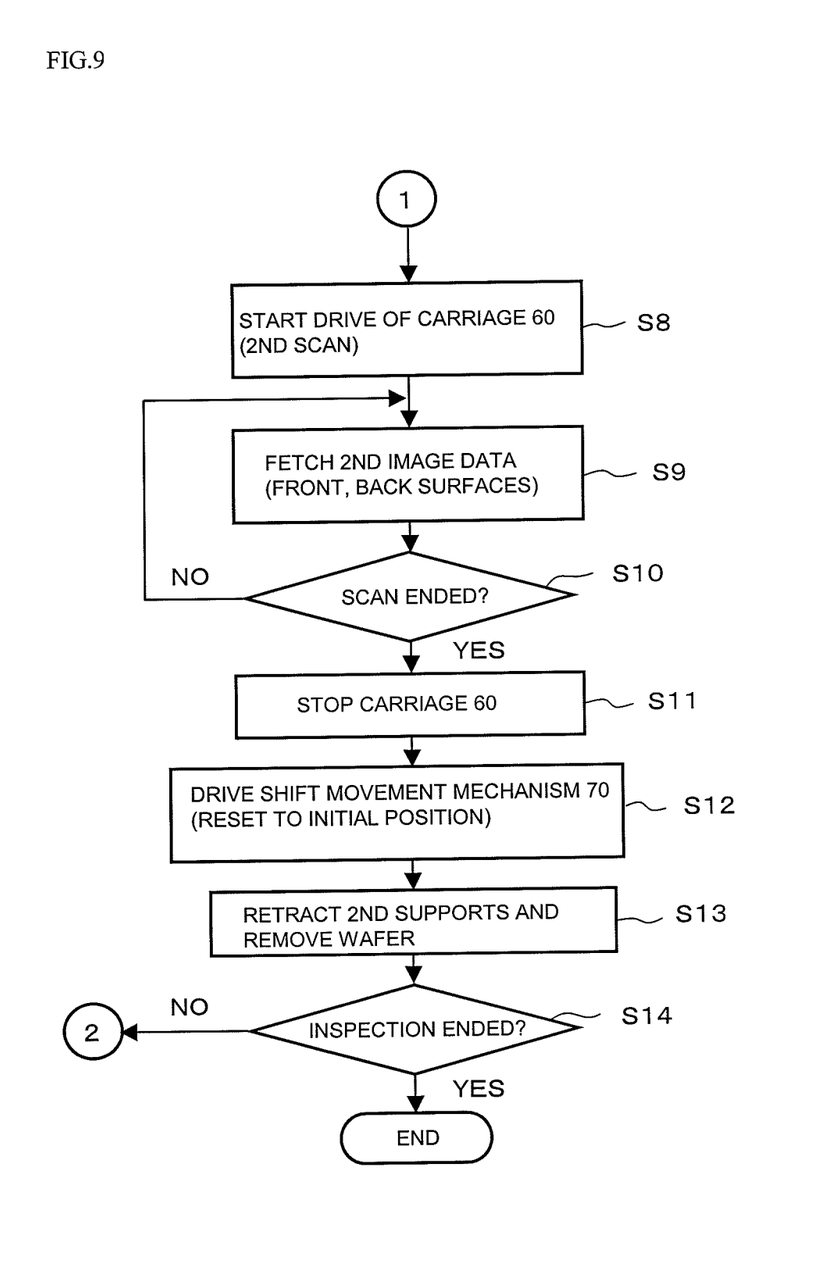
FIG. 9 A flow chart showing a processing routine at the processing unit (Part 2).

When the wafer 10 under inspection is supported by the second supports 24a to 24d of the support mechanism 20, the processing unit 100 shifts to the processing shown in FIG. 9 and instructs the start of the drive operation of the carriage 60 to the drive control unit 120 (S8). Under the control of the drive operation by the drive control unit 120 for the carriage 60 based on this instruction, the carriage 60 at the position of P3 is guided by the other scan direction guide grooves 52a, 52b and starts to move in a second direction D2 opposite to the first direction D1 at a predetermined speed (self powered movement). Further, along with the self powered movement of the carriage 60, the support mechanism 20 passes through the image capturing range E of the first camera unit 30a and second camera unit 30b (see FIG. 1). In the process, the first camera unit 30a and second camera unit 30b individually scan and capture images of the first surface and second surface of the wafer 10, supported by the support mechanism 20 (second supports 24a to 24d), in the scan direction Dsc2 (second scan).

Due to the scan in the scan direction Dsc2 of the first camera unit 30a and second camera unit 30b in the second relative position with respect to the support mechanism 20, the image capturing range Escn2 of the first surface and second surface of the wafer 10 (see FIG. 4 and FIG. 6) is captured. The first camera unit 30a and second camera unit 30b successively output image signals. The processing unit 100 receives as input the image signals from the first camera unit 30a and second camera unit 30b and successively stores the image signals as corresponding image data (second image data) in an internal memory (S9). The processing unit 100 judges if the carriage 60 has reached the shift direction guide groove 53 (P4 in FIG. 1) and the wafer 10 has finished being scanned. If so (S10, YES), it gives a stop instruction for the carriage 60 to the drive control unit 120 (S11). Under the control of the drive control unit 120 based on this stop instruction, the carriage 60 stops.

Figure 11:
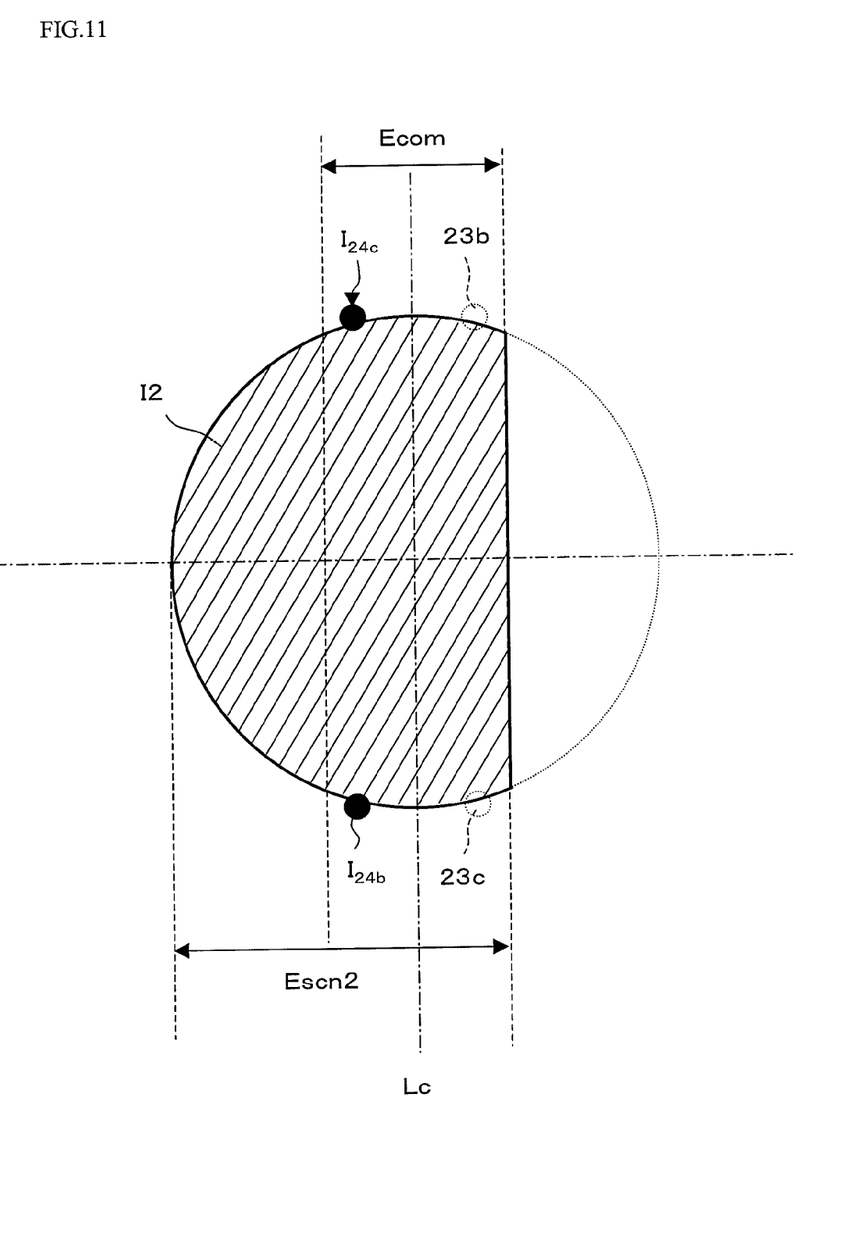
FIG. 11 A view showing an example of a captured image obtained when scanning a semiconductor wafer at a second relative position.

The second captured image I2 expressed by the second image data (corresponding to image capturing range Escn2) obtained by the imaging operation of the above-mentioned first camera unit 30a and second camera unit 30b, as shown in FIG. 11, has the second supports 24b, 24c arranged in the common image capturing range Ecom superimposed in it. Due to those image parts $I_{24b}$, $I_{24c}$, the second captured image I2 is partially obscured. That is, the portions at the wafer 10 supported by the second supports 24b, 24c are obscured by the images of the second supports 24b, 24c in this state. However, the first supports 23a to 23d of the support mechanism 20 are retracted in this state, so the second captured image I2 does not have the first supports 23b, 23c arranged at Ecom in the common image capturing range superimposed in it. Further, the other second supports 24a, 24d are arranged outside of the image capturing range Escn2, so these are also not superimposed in the second captured image I2.

Returning to FIG. 9, when the second image data finishes being acquired and the carriage 60 is stopped (S11), the processing unit 100 gives a drive instruction for the shift movement mechanism 70 to the drive control unit 120 (S12). Under the control of the drive operation by the drive control unit 120 for the shift movement mechanism 70 based on this instruction, the shift movement mechanism 70 (stage 71) moves in the second shift direction Dsft2 (see FIG. 1). Due to the movement of the carriage 60 accompanying the movement of this shift movement mechanism 70, the support mechanism 20 moves in the second shift direction Dsft2 while the support legs 22a, 22b are guided by the shift direction guide groove 53 until the first camera unit 30a and second camera unit 30b are positioned at the first relative position. When the support mechanism 20 reaches the scan direction guide grooves 51a, 51b and is reset to the initial position (see P1 in FIG. 1) and the first camera unit 30a and second camera unit 30b are positioned at the first relative position with respect to the support mechanism 20, the processing unit 100 instructs the removal of the wafer 10 to the drive control unit 120 (S13). Under the control of the drive operation by the drive control unit 120 for the second actuators 26a to 26d based on this instruction, synchronized with the removal mechanism of the wafer 10 (not shown), the second supports 24a to 24d retract and the support of the wafer 10 by the second supports 24a to 24d is ended. Further, the removal mechanism is used to remove the wafer 10 from the support mechanism 20.

When the first captured image I1 corresponding to the image capturing range Escn1 (including the common image capturing range Ecom) (see FIG. 10) and the second captured image I2 corresponding to the image capturing range Escn2 (including the common image capturing range Ecom) (see FIG. 11) are obtained for the first surface and second surface of the wafer 10 as explained above, the processing unit 100 combines these images and generates composite images of the surfaces of one wafer 1 (first surface and second surface). By using the images of the corresponding portions of the second captured image I2 for the portions of the first captured image I1 where the first supports 23b, 23c are superimposed and using the images of the corresponding portions of the first captured image I1 for the portions of the second captured image I2 where the second supports 24b, 24c are superimposed so as to generate the composite images, it is possible to obtain composite images in which neither of the supports are superimposed.

After this, the processing unit 100 judges if the imaging operation has ended, that is, judges if there are still wafers to be captured S14. Further, if there are wafers not yet captured S14, NO), the processing unit 100 returns to the processing shown in FIG. 8 and executes processing similar to the above on the next wafer (S1 to S7 and, FIG. 9, S8 to S14) once again. Further, each time a wafer 10 under inspection is given, processing similar to the above (FIG. 8 and FIG. 9) is executed. In the process, when it is judged that all wafers have finished being inspected S14, YES), the processing unit 100 uses the captured images of the wafers (composite images) to inspect the wafers.

According to the inspection apparatus explained above, it is possible to obtain a first captured image I1 where the first supports 23b, 23c are superimposed at portions corresponding to the common image capturing range Ecom of the wafer 10 by the first camera unit 30a and second camera unit 30b, but the other first supports 23a, 23d and second supports 24a to 24d are not superimposed (see FIG. 10). Further, it is possible to obtain a second captured image I2 where the second supports 24b, 24c are superimposed at portions corresponding to the common image capturing range Ecom, but the other second supports 24a, 24d and first supports 23a to 23d are not superimposed (see FIG. 11). For the portions in the first captured image I1 where the first supports 23b, 23c are superimposed, the states of the surfaces of the wafer 10 (first surface, second surface) are shown at the corresponding portions of the second captured image I2. Further, for the portions in the second captured image I2 where the second supports 24b, 24c are superimposed, the states of the surfaces of the wafer 10 (first surface, second surface) are shown at the corresponding portions of the first captured image I1. Since it is possible to generate composite images in which none of the supports are superimposed from the first captured image I1 and second captured image I2, even if capturing the image of the surface of a wafer 10 in a state using a plurality of supports to support its edges, the portions which the supports support can also be judged and analyzed in state from the captured images.

Further, according to the above-mentioned inspection apparatus, the support mechanism 20 supporting the wafer 10 only moves once back and forth over the base 50 (first direction D1, second direction D2) so as to simultaneously obtain two images of the first surface of the wafer 10 (first captured image I1, second captured image I2) and two images of the second surface (back), so the processing efficiency is good.

Note that the processing unit 100 can display composite images generated from the first image data and second image data on the display unit 112. Due to this, the operator can visually inspect the surface of the wafer 10. Further, the processing unit 100 can, as processing for inspection, perform processing on areas of the obtained composite images and thereby inspect the state of the treatment film formed on the surfaces of the wafer 10 or the state of damage, defects, etc. Further, when detected, it can also generate a map image displaying the coordinate values of the defect etc. on the composite images and display this on the display unit 112.

Note that the above-mentioned apparatus was designed to make the support mechanism 20 move relative to the first camera unit 30a and second camera unit 30b, but it is also possible to fix in place the support mechanism 20 and make the first camera unit 30a and second camera unit 30b move.

Further, the apparatus may also be configured with either of the first camera unit 30a and second camera unit 30b provided. In this case, it is possible to inspect one surface of the wafer 10 with edges supported by the plurality of supports. Further, if a wafer 10 inverting mechanism is provided (or manual inversion is performed), it is also possible to inspect the two surfaces of the wafer 10. Furthermore, the first camera unit 30a and the second camera unit 30b had line sensors as imaging devices, but the invention is not limited to this. For example, it is possible to provide area sensors as both imaging devices or possible to provide a line sensor for one and area sensor for another.

Further, the above-mentioned inspection apparatus generated composite images from the first captured image I1 and the second captured image I2, but such composite images need not necessarily be generated. In this case, it is possible to use the two captured images of the first captured image I1 and the second captured image I2 to inspect the state of a surface of the wafer 10 (first surface or second surface).

Further, the above-mentioned inspection apparatus scanned the surface of the wafer 10 twice to capture it, but it is possible to suitably set the number of scans in accordance with the size of the wafer and the image capturing ranges of the camera units. In this case, the mode of control of drive and stopping of the shift movement mechanism 70 and scan movement mechanism 60 can be suitably determined in accordance with the range of one scan, the number of scans, etc.

The above-mentioned apparatus drives the shift movement mechanism 70 and deploys and retracts the first supports 23a to 23d and second supports 24a to 24d by separate steps, but it is also possible to drive the shift movement mechanism 70 and deploy and retract the first supports 23a to 23d and second supports 24a to 24d simultaneously. By doing this, it is possible to shorten the imaging cycle.

Industrial Applicability

As explained above, the substrate surface inspection apparatus and substrate surface inspection method according to the present invention have the advantageous effect, even when using a plurality of supports to support the edges of a substrate and capturing an image of its surface in that state, of enabling the state of even portions supported by the supports to be judged and analyzed from the captured images. These are useful as a substrate surface inspection apparatus and substrate inspection method capturing an image of the surface of a semiconductor wafer or other substrate for inspection.

The invention claimed is:

1. A substrate surface inspection apparatus capturing an image of a surface of a substrate and inspecting said substrate based on the obtained image, said substrate surface inspection apparatus having:
   a support mechanism provided with a plurality of first supports and a plurality of second supports able to support edges of said substrate and release the same,
   an imaging unit arranged facing the surface of said substrate, said substrate being supported by either said plurality of first supports or said plurality of second supports in said support mechanism,
   a scan movement mechanism making said imaging unit and said support mechanism move relative to each other so that said imaging unit scans and captures an image of the surface of said substrate in a predetermined scan direction,
   shift movement mechanism making said imaging unit and said support mechanism relatively move in a direction traversing said scan direction between a first relative position at one end of the move and a second relative position at the other end of the move;
   said imaging unit able to capture,
   when said imaging unit and said support mechanism are at said first relative position, a first image from a predetermined region at one side of said substrate, said first image defining a first image capturing range, and
   when said imaging unit and said support mechanism are at said second relative position, a second image from a predetermined region at the other side of said substrate, said second image defining a second image capturing range;
   said first and second image capturing range including a common image capturing range and said common image capturing range defined as a predetermined range of said substrate in a direction perpendicular to said scan direction;
   wherein at least one of said plurality of first supports in said support mechanism is positioned outside the first image capturing range and at least another one of said plurality of first supports in said support mechanism is positioned inside said common image capturing range;
   wherein at least one of said plurality of second supports in said support mechanism is positioned outside the second image capturing range and at least another one of said plurality of second supports in said support mechanism is positioned inside said common image capturing range;
   a first mechanism for releasing said plurality of first supports from supporting edges of said substrate in the step of capturing the second image wherein said substrate is supported by said plurality of second supports, and
   a second mechanism for releasing said plurality of second supports from supporting edges of said substrate in the step of capturing the first image wherein said substrate is supported by said plurality of first supports.

2. A substrate surface inspection apparatus as set forth in claim 1, wherein said imaging unit is set fixed in position, and said scan movement mechanism makes said support mechanism move in a direction opposite to said scan direction.

3. A substrate surface inspection apparatus as set forth in claim 2, wherein said shift movement mechanism makes said support mechanism move between said first relative position and said second relative position.

4. A substrate surface inspection apparatus as set forth in claim 1, wherein said imaging unit has a line sensor extending in a direction traversing said scan direction.

5. A substrate surface inspection apparatus as set forth in claim 1, wherein said imaging unit has a first camera unit arranging facing a first surface of said substrate supported by either of said plurality of first supports and said plurality of second supports of said support mechanism and a second camera unit arranged facing a second surface of said substrate forming a back side of said first surface.

6. A substrate surface inspection apparatus as set forth in claim 5, wherein
   said apparatus has a first illumination unit illuminating an image capturing location of said first camera unit and a second illumination unit illuminating an image capturing location of said second camera unit, and
   said first illumination unit and said second illumination unit are set so that an illumination direction of light from said first illumination unit does not face said second camera unit and an illumination direction of light from said second illumination unit does not face said first camera unit.

7. The substrate surface inspection apparatus as set forth claim 1, wherein said scan movement mechanism is configured such that the scan direction of said imaging unit with respect to said substrate when capturing the first image and the scan direction of said imaging unit with respect to said substrate when capturing the second image are set to be opposite.

* * * * *